US00PP08771P

United States Patent [19]

Fruehwirth

[11] Patent Number: Plant 8,771

[45] Date of Patent: Jun. 7, 1994

[54] POINSETTIA PLANT "490 JINGLE BELLS"

[75] Inventor: Franz Fruehwirth, Encinitas, Calif.

[73] Assignee: Paul Ecke Ranch, Inc., Encinitas, Calif.

[21] Appl. No.: 57,962

[22] Filed: May 4, 1993

[51] Int. Cl.[5] ..... A01H 5/00

[52] U.S. Cl. ..... Plt./86.1

[58] Field of Search ..... Plt. 88.1

*Primary Examiner*—James R. Feyrer

*Attorney, Agent, or Firm*—Arnold, White & Durkee

[57] ABSTRACT

Poinsettia "490 Jingle Bells" is a new cultivar, distinguished by bicolored red and pink bracts and intense dark green foliage with self-branching characteristics, "490 Jingle Bells" is a color sport of the dark red bracted '490' (U.S. Plant Pat. No. 7825) with the same early flowering response and cultural requirements. The new plant produces a very desirable branched flowering pot plant. The new plant is resistant to epinasty after being confined to shipping containers and recovers rapidly if the plant does become epinastic. The post-production foliage and bract retention is excellent even under low light intensities in the consumer's home.

1 Drawing Sheet

BACKGROUND OF THE NEW PLANT

This new poinsettia cultivar originated as an induced bicolored red and pin bracted sport of 490 (U.S. Plant Pat. No. 7825) in my greenhouse in Encinitas, Calif. It was induced by irradiation of 100 vegetative plants of '490' with 4,000 rads of radiation randomly applied to the whole plant without lethal effect. Of the 100 plants irradiated, one was found with a color mutation. The mutant had red and pink flower bracts. The bract color in combination with early flowering, self branching, red and pink flower bracts and dark green foliage; traits which help distinguish it from other poinsettia cultivars, and seem to make it a desirable plant for commercial greenhouse production. After selection, "490 Jingle Bells" was vegetatively reproduced from stem cuttings for test purposes in Encinitas, Calif. By subjecting clones of this plant to successive generations of vegetative propagation, it was demonstrated that the distinctive characteristics of "490 Jingle Bells" held true from generation to generation. Other than bract color, the new plant '490 Jingle Bells' was similar in height, leaf color, leaf shape and other characteristics to the parent plant '490'.

DESCRIPTION OF THE PHOTOGRAPH

Poinsettia "490 Jingle Bells" is illustrated in the accompanying color photographs. The photo shows a side view of 3 single stem plants per pot in full flower. Evidence of self branching can be seen in the flowering axillary branches beneath the upper canopy of bracts.

DESCRIPTION OF THE PLANT

The following is a detailed description of this new poinsettia as observed in Encinitas, Calif., U.S.A. during December 1992. Observations were recorded from flowering plants, grown as 3 single stem plants per pot. The pot was 14 cm in diameter and 11 cm in height. Color designations are compared to the 1986 edition of R.H.S. Colour Chart, first published in 1966 by The Royal Horticultural Society, London, England.

THE PLANT

Origin: Sport of '490' (U.S. Plant Pat. No. 7,825), induced through irradiation of vegetative plants with 4000 rads of radiation.

Classification:

*Botanic.*—*Euphorbia pulcherrima* Willd.

*Common name.*—Poinsettia.

*Cultivar name.*—"490 Jingle Bells".

Form: Shrub.

Height: Short.

Growth habit: As a single stemmed plant, upright and short with self-branching side shoots. The application of a chemical growth retardant may not be needed to restrict height for commercial pot plant production. 3 unpinched plants in a pot with an overall height of 37 cm and an overall width of 48 cm were observed. The bract diameter of individual flowers was 33 cm.

Branching: Axillary branches will develop and terminate in a flower without pinching. However, it is usually desirable to pinch "490 Jingle Bells" and remove all terminal dominance. Then, all axillary branches will develop uniformly and at a faster rate.

Growth rate: Rooting of stem cuttings occurs in 12–18 days under intermittent mist.

Flowering: The plant will flower in about eight weeks under continuous long night conditions and night temperatures of about 16–18 degrees C. Like its parent ('490'), "490 Jingle Bells" will be in full bloom in mid-November in the northern hemisphere under natural daylength conditions. "490 Jingle Bells" flowers earlier than most known poinsettias because flower induction seems to occur in mid-September, about 10 days earlier than normal.

Foliage: At flowering, plants were observed with 15 uniformly dark green leaves, one leaf per node. The leaves were of Medium size, leaf blades typically being 12–13 cm. long and 8–9 cm. wide with leaf petioles 6–7 cm. long. Between the green leaves and the true flower bracts were 4 transitional bracts from the uppermost nodes on each stem. These leaf/bracts were green but changed to red and pink as the flowers matured. At maturity, one or two of these leaf/-bracts were not completely red and pink but retained some green coloration along the midvein and margins as seen in the photograph.

*Leaf shape.*—Typical leaves are generally ovate with obtuse bases and acuminate tips. Leaf margins are mostly entire.

*Color.*—Upper side — Dark green, darker than RHS 139A. Under side — Green, near RHS 147B.

Bracts: Generally there were 15–18 bicolored red and pink bracts of various sizes subtending the cyathia. The primary bracts have blades typically 12–13 cm long and 10–11 cm wide with petioles about 5 cm long.

*Shape.*—Primary bracts are ovate with acute bases and acuminate tips and weakly lobed with 1 small indentation on either side of the bract. Secondary bracts are obovate to elliptic and have entire margins.

*Color.*—Upper side — Bicolored. Dark red bracts with irregularly shaped pink splotches. Red color of small bracts near RHS 45B. Older, larger tracts "blue" with age to near RHS 53B. Pink areas are between RHS 48C-D. Under side — Bicolored. Red areas darker than RHS 47A. Pink areas near RHS 48D.

Flowers:

*Cyathia.*—Generally, 16–18 cyathia (flowers) were present when the plant was in full bloom. Each cyathium was about 7 mm long and 6 mm wide, green in color, and fringed with red at the distal end. A yellow nectar cup protrudes from the side of each cyathium. The flower pedicel is also green and about 4 mm in length. The stamens protruding from the cyathia are red. The anthers are bifurcate with copious yellow pollen. Stigmas are dark red and trifurcate. Cyathium retention in three weeks after the plant is in full bloom.

*Nectar exudate.*—Abundant.

*Seeds.*—Self-incompatible.

*Fertility.*—Not observed.

Post production: "490 Jingle Bells" is resistant to epinasty after being confined to shipping containers and recovers rapidly if the plant does become epinastic. The foliage and bract retention is excellent even under low light intensities in the consumer's home.

What is claimed is:

1. A new and distinct Poinsettia cultivar, substantially as herein shown and described, distinguished by its intense dark green foliage, bicolored red and pink bracts, and resistance to epinasty.

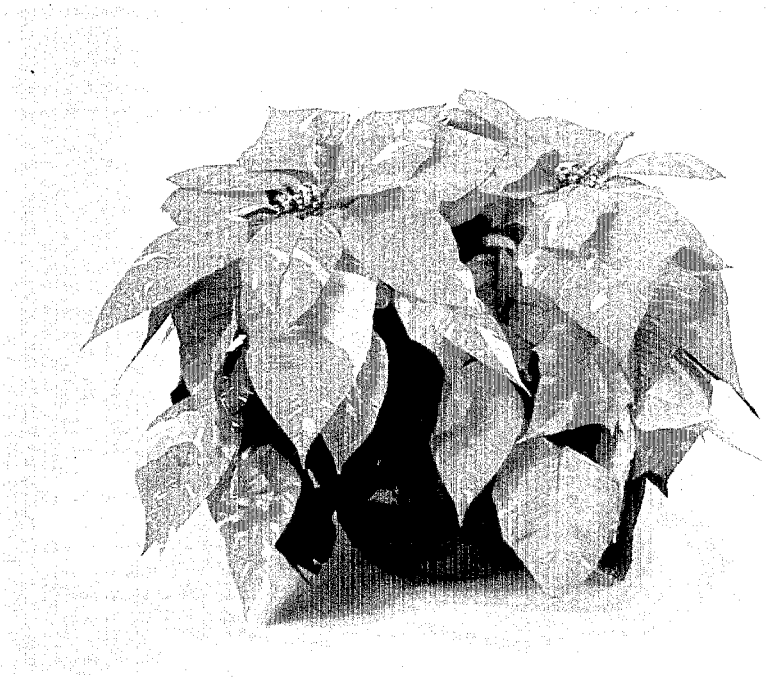

* * * * *